US012793836B2

(12) United States Patent
Kowarschik

(10) Patent No.: US 12,793,836 B2
(45) Date of Patent: Nov. 10, 2026

(54) IMAGE PROCESSING METHOD, MEDICAL IMAGING SYSTEM, COMPLETE MEDICAL SYSTEM AND PROCESSING METHOD

(71) Applicant: Siemens Healthcare GmbH, Erlangen (DE)

(72) Inventor: Markus Kowarschik, Nuremberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 449 days.

(21) Appl. No.: 17/850,704

(22) Filed: Jun. 27, 2022

(65) Prior Publication Data

US 2022/0415483 A1 Dec. 29, 2022

(30) Foreign Application Priority Data

Jun. 29, 2021 (DE) ..................... 10 2021 206 748.4
May 18, 2022 (DE) ..................... 10 2022 204 959.4

(51) Int. Cl.
*G16H 30/40* (2018.01)
*G06T 7/00* (2017.01)

(52) U.S. Cl.
CPC ........... *G16H 30/40* (2018.01); *G06T 7/0012* (2013.01); *G06T 2207/10116* (2013.01)

(58) Field of Classification Search
CPC .................. G16H 30/40; G06T 7/0012; G06T 2207/10116; G06T 5/70; G06T 2207/10081; G06T 2207/20092; G06T 2207/30168; G06T 5/50
See application file for complete search history.

(56) References Cited

U.S. PATENT DOCUMENTS

| | | | | |
|---|---|---|---|---|
| 10,945,688 | B2 * | 3/2021 | Cao | A61B 6/4241 |
| 2013/0343624 | A1 * | 12/2013 | Thibault | G06T 11/006 382/131 |
| 2019/0108618 | A1 * | 4/2019 | Hwang | G06T 3/4046 |
| 2019/0122330 | A1 * | 4/2019 | Saget | A61F 2/461 |
| 2020/0094072 | A1 | 3/2020 | Ritter | |

FOREIGN PATENT DOCUMENTS

| | | | |
|---|---|---|---|
| DE | 102018216370 | A1 | 3/2020 |
| WO | WO 2018148464 | A1 | 8/2018 |

* cited by examiner

*Primary Examiner* — Ming Y Hon
*Assistant Examiner* — Amanda H Pearson
(74) *Attorney, Agent, or Firm* — Harness, Dickey & Pierce, P.L.C.

(57) ABSTRACT

A method for recording and processing image sensor data of an examination object that can be created by a medical imaging system, having the following steps: recording image sensor raw data of the examination object by way of an image detector of the imaging system, processing the image sensor raw data, wherein from the image sensor raw data, two resultant image datasets of the same examination object differing with regard to the image quality are created, wherein the image quality of a first resultant image dataset is configured for a human perception and the image quality of a second resultant image dataset is configured for a further processing by machine, and outputting the first resultant image dataset to a display unit and passing on the second resultant image dataset to an interface for further processing by machine.

20 Claims, 4 Drawing Sheets

IMAGE PROCESSING METHOD, MEDICAL IMAGING SYSTEM, COMPLETE MEDICAL SYSTEM AND PROCESSING METHOD

CROSS-REFERENCE TO RELATED APPLICATION(S)

The present application hereby claims priority under 35 U.S.C. § 119 to German patent application numbers DE 102021206748.4 filed Jun. 29, 2021 and DE 102022204959.4 filed May 18, 2022, the entire contents of each of which are hereby incorporated herein by reference.

FIELD

At least some example embodiments of the present invention relate to a method for recording and processing image sensor data of an examination object that can be created by a medical imaging system, a medical imaging system for carrying out a method of this type and a medical system and a method for recording and processing sensor data.

BACKGROUND

Medical image data which is recorded and processed by medical imaging systems and is processed by machine (that is, for example, by learning-based approaches, AI-based, data-driven) or by conventional analytical approaches, must often meet other criteria with regard to image quality than image data which is observed, analyzed or evaluated by human operators. Such criteria relate, for example, to the noise behavior, the contrast dynamics, the image sharpness and the spatial resolution of the image data. Human users—who are often physicians, for example, diagnostic or interventional radiologists, or surgeons—can vary the preferences greatly in relation to the image impression. Accordingly, image data processed for a human user is generally less suitable for further processing by machine.

A further processing by machine can be necessary, for example, in the field of interventional treatments in which medical objects are navigated in the body of the patient under 2D fluoroscopic monitoring and must be recognized automatically, or in the automatic recognition of anatomical landmarks, lesions, vascular occlusions or tumors.

SUMMARY

In order to provide image data which is suitable both for processing by machine and also meets the requirements of a human user, due to the contradictory requirements, compromises often are made, which have the consequence that the resulting image data is not particularly well suited to any of the requirements. As a result, errors can arise both in the processing by machine and also the human perception, and thus finally the quality of the diagnosis can be impaired. On that basis, the resultant therapy cannot be carried out optimally for the patient.

Example embodiments of the present invention provide a method for recording and processing image sensor data which overcomes the disadvantages of the prior art; and provide an imaging system suitable for carrying out the method.

According to at least one example embodiment, a method for recording and processing image sensor data of an examination object that is able to be generated by a medical imaging system, includes recording image sensor raw data of the examination object using an image detector of the imaging system; processing the image sensor raw data, wherein from the image sensor raw data, two resultant image datasets of the same examination object differing with regard to the image quality are created, an image quality of a first resultant image dataset is configured for a human perception and an image quality of a second resultant image dataset is configured for further processing by a machine; outputting the first resultant image dataset to a display unit; providing the second resultant image dataset to an interface for further processing by a machine; and using a processing result arising from the second resultant image dataset, the processing result being generated from the further processing by the machine.

According to at least one example embodiment, an image sensor raw dataset is recorded and the first resultant dataset and the second resultant image dataset are generated from the same recorded image sensor raw dataset using two different image processing methods.

According to at least one example embodiment, two image sensor raw datasets of the same examination object are recorded in the same examination situation with different recording parameters, a first image processing method generates a first resultant image dataset from the first image sensor raw dataset and a second image processing method generates a second resultant image dataset from the second image sensor raw dataset.

According to at least one example embodiment, the imaging system includes an X-ray device and the image detector includes an X-ray detector.

According to at least one example embodiment, the recording parameters are based on at least one of an X-ray voltage, an X-ray current, a pulse width of the X-ray pulse of an X-ray source, a filter setting of an X-ray collimator, a zoom setting of an image system, or a recording frequency.

According to at least one example embodiment, the image quality of at least one of the first resultant image dataset or the second resultant image dataset is determined by at least one of a signal-to-noise ratio, a contrast dynamic, an image sharpness, a spatial resolution, or an edge sharpness.

According to at least one example embodiment, the medical imaging system includes an angiography X-ray system, a fluoroscopy X-ray system, a computed tomography system, a magnetic resonance tomography system or an ultrasonic system.

According to at least one example embodiment, a medical imaging system is configured to perform a method according to example embodiments of the present invention, the medical imaging system including a control unit configured to control the imaging system; an image sensor configured to record the image sensor raw data of the examination object; a processing unit configured to process the image sensor raw data to the first resultant image dataset and the second resultant image dataset; the display unit configured to output the first resultant image dataset; and a unit configured to perform the further processing.

According to at least one example embodiment, the control unit is configured to control at least some functions of the imaging system automatically.

According to at least one example embodiment, a complete medical system including an imaging system configured to perform a method according to example embodiments of the present invention and a robot system configured to navigate an instrument in a hollow organ of a patient and image-monitored by the imaging system, the complete medical system comprising a control unit configured to control the imaging system; an image sensor configured to record the image sensor raw data; a processing unit configured to process the image sensor raw data to the first resultant image dataset the second resultant image dataset; a robot control system configured to control a robot-assisted drive system; an input unit configured to receive an input; the display unit configured to output the first resultant image dataset; and a unit configured to perform the further processing using a machine learning algorithm, wherein the further processed data is used for controlling the navigation.

According to at least one example embodiment, a method for recording and processing sensor data that is able to be created by a complete medical system includes recording sensor raw data using a sensor apparatus of the complete medical system; processing the sensor raw data, wherein from the sensor raw data, two resultant image datasets of the same examination situation differing with regard to the signal quality are created, an signal quality of a first resultant image dataset is configured for a human perception and an image quality of a second resultant image dataset is configured for a further processing by machine; outputting the first resultant image dataset to a display unit; providing the second resultant image dataset to an interface for further processing by a machine; and using a further processing result arising from the second resultant image dataset, the further processing result being generated from the further processing by the machine.

According to at least one example embodiment, the first and the second resultant dataset are generated using two different processing procedures.

BRIEF DESCRIPTION OF THE DRAWINGS

Example embodiments of the present invention and further advantageous embodiments, in accordance with features of the subclaims, will now be described in greater detail on the basis of exemplary embodiments illustrated schematically in the drawings, but without any restriction of the present invention to these exemplary embodiments arising therefrom. In the figures:

DETAILED DESCRIPTION

Figure 1:
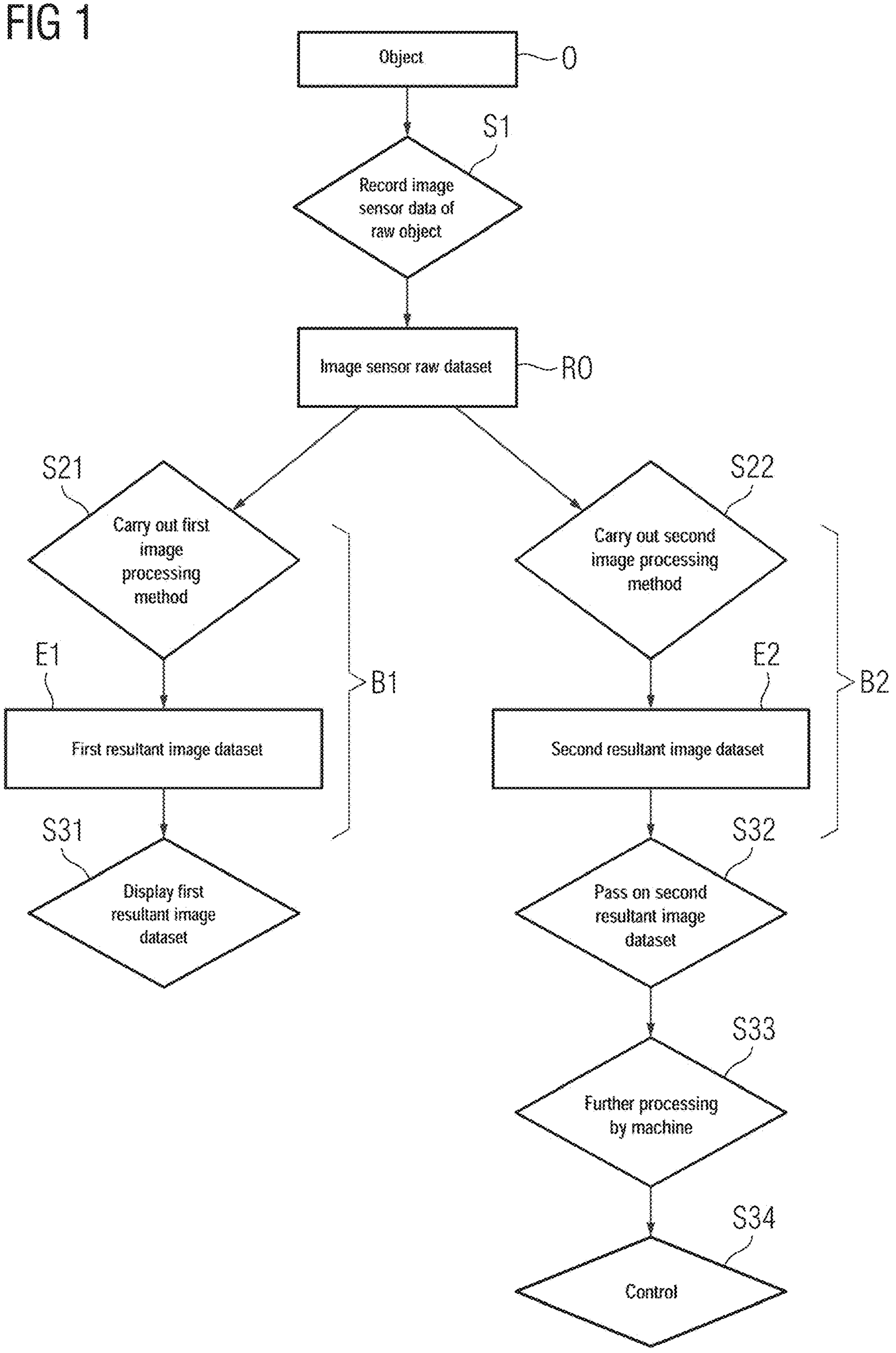
FIG. 1 is an illustration of a method according to an example embodiment.

Example embodiments of the present invention provide a method for recording and processing image sensor data of an examination object that can be created by a medical imaging system according to claim 1, a medical imaging system according to claim 8, a complete medical system according to claim 10 and a method for recording and processing sensor data that can be created by a complete medical system according to claim 11. Advantageous embodiments of the present invention are the subject matter of the associated subclaims.

The method according to example embodiments of the present invention for recording and processing image sensor data of an examination object that can be created by a medical imaging system comprises the following steps: recording image sensor raw data of the examination object by way of an image detector of the imaging system, processing the image sensor raw data, wherein from the image sensor raw data, two resultant image datasets of the same examination object differing with regard to the image quality are created, wherein the image quality of a first resultant image dataset is configured for a human perception and the image quality of a second resultant image dataset is configured for a further processing by machine, and outputting the first resultant image dataset to a display unit and passing on the second resultant image dataset to an interface for further processing by machine and using a processing result arising from the second resultant image dataset by way of further processing by machine for controlling the medical imaging system or another medical system associated with the medical imaging system. By way of the method according to example embodiments of the present invention, an adaptation of medical image data to the requirements of a human user independently of the quality of the results of the processing by machine, and vice versa, is possible.

The method according to example embodiments of the present invention thereby minimizes the error-proneness of the resultant image datasets to be further processed, with regard both to the human observer, and also the further processing by machine (e.g. by way of a machine learning algorithm, AI-based, data-driven). By way of the image processing dedicated to the corresponding further use, it is possible to obtain an optimum image quality for the respective usage purpose, so that the best possible diagnosis and, dependent thereupon, treatment can be obtained for a patient.

A resultant image dataset (that is e.g. an image or an image sequence in 2D or 3D) configured with regard to the image quality for human perception should herein be understood as meaning that the features mapped on the image are particularly accessible to human perception capabilities both in their details and also their overall impression. This can also differ in parts, as described above, from observer to observer. In general, this is achieved by way of image processing methods such as noise removal (smoothing), edge sharpening, contrast optimization (e.g. by histogram stretching), etc.

According to one embodiment of the present invention, the image quality is determined by criteria such as a signal-to-noise ratio and/or a contrast dynamic and/or an image sharpness and/or a spatial resolution and/or an edge sharpness, for instance. It can thus be provided, for example, that a low noise level optimized for an observation by a user can have a relatively low spatial resolution and a relatively low image sharpness. A user can select a setting of this type of the image quality optimized for his observation, for example he can select it before the method, or a setting optimized for an average user is used.

A resultant image dataset configured with regard to image quality for further processing by machine should be understood herein to mean that the image data captured can be captured and processed optimally for a machine algorithm. This can mean, for example, that a more intense noise level and thus also a higher spatial resolution and image sharpness are set. The processing results arising from the second resultant image dataset by way of further processing by machine are then used for controlling the imaging system or another system. Thus, for example, following analysis of the second resultant image dataset by machine with regard to a recognition of body regions, an automatic setting of a suitable acquisition protocol or a dose-efficient collimation in the imaging system is carried out. When a navigation system is used for the navigation of an object through a hollow organ, the further processed data can be used for controlling the navigation system.

According to an example embodiment of the present invention, an image sensor raw dataset is recorded and then, from the same recorded image sensor raw dataset, the first and the second resultant image dataset are generated by way of two different, mutually independent image processing methods. Herein, therefore, from the same image sensor raw dataset, by way of different image processing methods, different resultant image datasets are generated, wherein the first is optimized for a perception by a human user and the second for the further processing by machine. This alternative has the advantage that only one single image sensor raw dataset has to be recorded. In radiation-utilizing imaging systems, e.g. X-ray systems, the dose can herein be reduced and the patient protected.

According to another example embodiment of the present invention, two image sensor raw datasets of the same examination object are recorded in the same examination situation with different recording parameters and, from the first image sensor raw dataset, by way of a first image processing method, a first resultant image dataset and from the second image sensor raw dataset, by way of a second image processing method, a second resultant image dataset is generated, wherein the first is optimized for an observation by a human user and the second for the further processing by machine. For an imaging system designed as an X-ray system with an X-ray detector, in particular, the recording parameters of an X-ray voltage and/or an X-ray current and/or a pulse width (duration of the pulse) of the X-ray pulse from an X-ray source and/or a filter setting of an X-ray collimator and/or a zoom setting of an image system and/or a recording frequency can be formed. In this alternative, therefore, as early as during the recording, a distinction is made between human perception and further processing by machine and image sensor raw datasets independent of one another are generated, in particular as far as possible simultaneously or with a slight temporal offset. The recording can take place, for example, alternatingly or according to a previously defined protocol. By way of this alternative, the resultant image datasets can be still better adapted to the intended use. From the X-ray voltage and/or the X-ray current and/or the pulse width, there results, for example, the X-ray dose. The filter setting should be understood, for example, to be the use of special filters such as copper or tin filters for beam hardening, a use of transparency filters for different image regions or a general beam shaping.

According to a further embodiment of the present invention, the medical imaging system is formed by an angiography X-ray system, a fluoroscopy X-ray system, a computed tomography system, a magnetic resonance tomography system or an ultrasonic system. The method is usable with all the possible radiation-based or non-radiation-based imaging systems.

In addition, in the context of example embodiments of the present invention, a medical imaging system is provided for recording and processing image sensor data of an examination object for carrying out a method described above, having a control unit for controlling the imaging system, an image sensor for recording sensor raw data of an examination object, a processing unit for processing the image sensor raw data to a first resultant image dataset configured for a human perception and a second resultant image dataset configured for further processing by machine, a display unit for output of the first resultant image dataset and a unit for further processing by machine of the second resultant image dataset. The control unit is provided for controlling the imaging system using a processing result arising from the second resultant image dataset by way of further processing by machine. The imaging system is formed, for example, by an X-ray system (fluoroscopy X-ray system, angiography X-ray system, computed tomography system etc.) with an X-ray source and an X-ray detector.

Example embodiments of the present invention also relate to a method for recording and processing sensor data that can be created by a complete medical system, having the following steps: recording sensor raw data by way of a sensor apparatus of the complete medical system, processing the sensor raw data, wherein from the sensor raw data, two resultant datasets of the same examination situation differing with regard to the signal quality are created, wherein the signal quality of a first resultant dataset is configured for a human perception and the image quality of a second resultant dataset is configured for a further processing by machine, and outputting the first resultant dataset to a display unit and passing on the second resultant dataset to an interface for further processing by machine and using a processing result arising from the second resultant dataset by way of further processing by machine for controlling the complete medical system or another medical system associated with the complete medical system.

In order to satisfy different requirements regarding the image quality of image data, it is proposed in the context of example embodiments of the present invention to provide, independently of one another, a first resultant image dataset which meets the requirements of a human user, and a second resultant image dataset that is suitable for processing by machine.

FIG. 1 shows the steps of a first alternative of the method for recording and processing image sensor data of an examination object that can be created by a medical imaging system. The imaging system can be, for example, a fluoroscopy X-ray system which records 2D fluoroscopy images by an X-ray detector. The fluoroscopy images serve for monitoring and an automatic or semi-automatic navigation of a medical instrument (e.g. guide wire, catheter, etc.) through a hollow organ of the patient. A navigation of this type can be carried out by a robot system (e.g. the CorPath GRX system from Corindus, Inc.) in which a robot system is connected between the hands of the treating person and the patient, with the advantage that the treating person carries out the maneuvering of the objects by remote control. In order to carry out, for example, an endovascular intervention (e.g. for the purpose of recanalization after an acute cardiac infarction or an acute ischemic stroke), on the basis of 2D fluoroscopy images, an automatic localization of the medical instrument is performed by a further processing unit with a machine learning algorithm. The position and/or orientation of the medical instrument recognized thereby is used for the further navigation.

Starting with an examination object O, in the present example, a hollow organ of a patient with an instrument situated therein, in a first step S1 at a first time point, image sensor raw data is recorded and therefrom, an image sensor raw dataset RO is obtained in the form of a fluoroscopy raw dataset. The image sensor raw dataset RO is then fed into two different mutually independent image chains B1; B2. Thus, in a second step S21 of the first image chain B1, a first image processing method is carried out and therefore a first resultant image dataset E1 is generated in the form of a first fluoroscopy resultant image dataset. The first image processing method itself can contain one or a plurality of different processing steps which, for the sake of simplicity, are summarized here. The individual steps can comprise a noise-reduction, a contrast processing, a filtration, a transformation etc. After carrying out the first image processing method, from the image sensor raw dataset RO, there results the first resultant image dataset E1 which is configured and/or optimized for a human perception. Exactly how a first image processing method looks, by which a first resultant image dataset E1 is obtained can be specified, for example, before the method, and it can also be set user-specifically. Overall, the features mentioned are particularly readily available to human perception capabilities in their details and also their overall impression. It can be provided, for example, that a 2D fluoroscopy image optimized for observation by a user has a substantially low noise level and also a substantially low spatial resolution and a substantially low image sharpness. A user can select a setting of this type of the image quality optimized for his observation, for example he can select it before the method, or a setting optimized for an average user is used.

In a third step S22 of the second image chain B2, a second image processing method is carried out and thereby a second resultant image dataset E2 is generated in the form of a second fluoroscopy resultant image dataset. The second image processing method itself can contain one or a plurality of different processing steps which, for the sake of simplicity, are also summarized here. The individual steps can comprise, for example, a noise-reduction, a contrast processing, a filtration, a transformation etc. The second resultant image dataset E2 resulting from the image sensor raw dataset RO after carrying out the second image processing method is configured and/or optimized for further processing by machine. This means that the captured image data can be captured and processed optimally for a machine algorithm. This can mean, for example, that the second resultant image dataset E2 has a substantially high level of noise but also a substantially high spatial resolution and a substantially high image sharpness.

If both the resultant image datasets are present, subsequently in a fourth step S31, in the context of the first image chain B1, the first resultant image dataset E1 is displayed—in the current example, as a fluoroscopy image—on a display unit, for example a monitor or a touch display. In this way, a user can observe and evaluate the image, for example, the fluoroscopy image and, if needed, carry out further actions.

In a fifth step S32 in the context of the second image chain B2, the second resultant image dataset E2 is passed on to an interface for further processing by machine in order to be fed to a unit for further processing by machine, said unit having, for example, a machine learning algorithm. In the present example, such a machine algorithm can comprise an automatic object and/or edge recognition of the navigated instrument. In an eighth step S33, in the context of the second image chain B2, the further processing by machine then takes place, that is, for example the automatic object and/or edge recognition of the navigated instrument. The processing result arising from the further processing by machine is then used in a ninth step S34 for controlling the robot system, thus for example, the position of the navigated instrument is used for the further navigation such that the navigated path is continued or changed.

Figure 2:
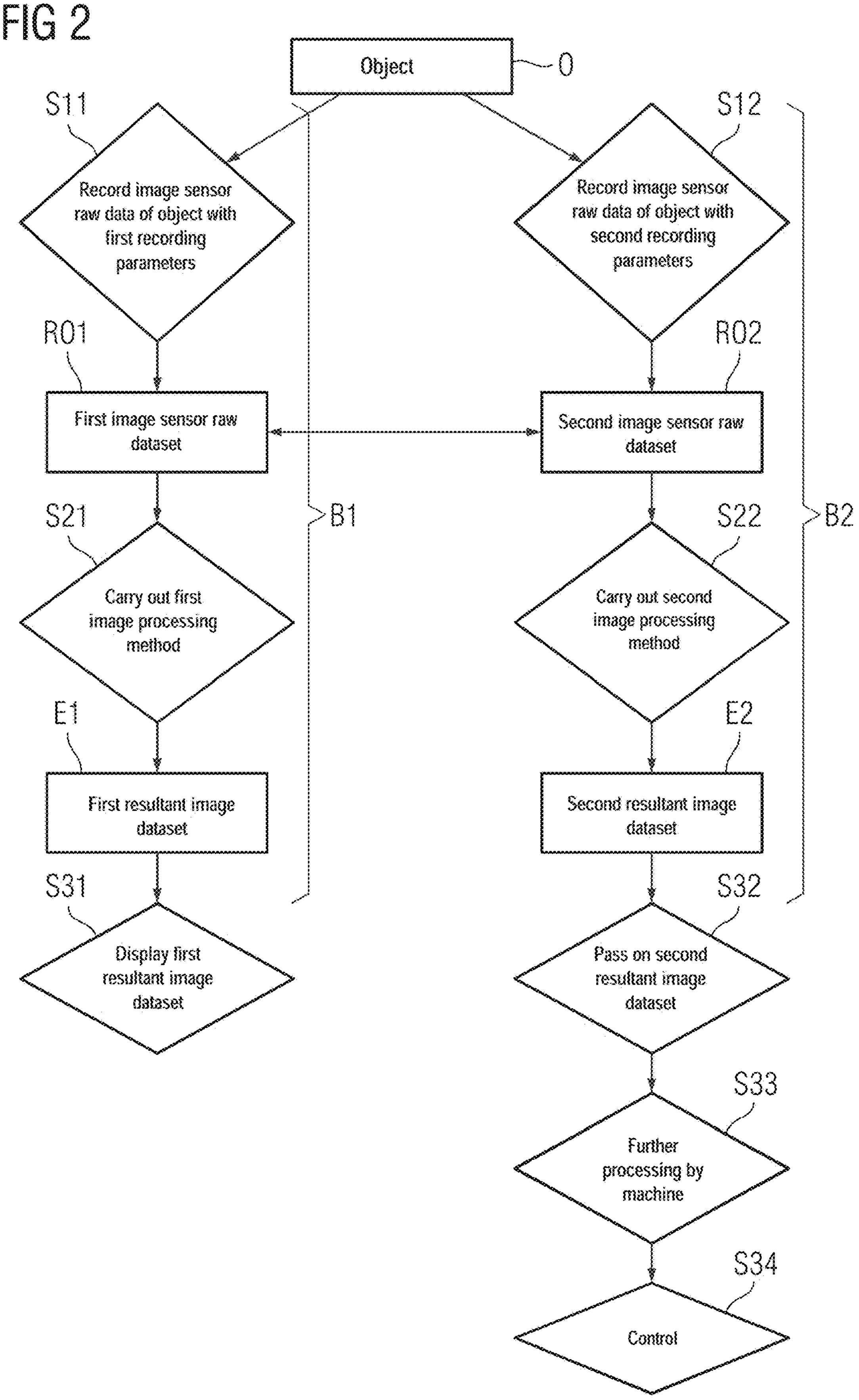
FIG. 2 is an illustration of a method according to another example embodiment.

FIG. 2 shows the steps of a second alternative of the method for recording and processing image sensor data of an examination object that can be created by a medical imaging system. The imaging system can be, for example, a 3D X-ray system which records a plurality of projection images from different projection directions by an X-ray detector and reconstructs them to a 3D volume image. A 3D X-ray system of this type can have, for example, an adjustable C-arm with an X-ray source and an X-ray detector. Such 3D volume images are constructed, for example, for diagnosis in the event of fractures to bone structures or tumors on organs. Apart from a manual diagnosis by a physician, an automatic recognition of anatomical landmarks and/or lesions can also be performed in order to be able to produce comprehensive treatment suggestions. In the second alternative of the method, a first image chain B1 and a second image chain B2 are run through independently of one another.

Starting from an examination object O, in a sixth step S11, the first image chain B1 (optimized for human perception), a first image sensor raw dataset RO1 of the examination object O is recorded in a particular examination situation with first recording parameters. Close in time to this recording (e.g. directly before or after it or in an alternating recording protocol) in a seventh step S21 of the second image chain B2 (optimized for further processing by machine) a second image sensor raw dataset RO2 of the examination object O is recorded in the same examination situation with second recording parameters. The first and the second recording parameters are different from one another. For an X-ray system with an X-ray detector, in particular, the recording parameters of a radiation dose and/or an X-ray voltage and/or an X-ray current of an X-ray source and/or a filter setting of an X-ray collimator and/or a zoom setting of an image system and/or a recording frequency can be formed or differences can exist in the recording duration. It can thus be provided that the recording parameters are distinguished for a further processing by machine in having a substantially low dose (from the X-ray current and the X-ray voltage) and for this purpose, a substantially small zoom. For the human user, a substantially high zoom (user wishes to zoom in) and thus a substantially higher X-ray dose (due to a lower noise level) is used.

After the recordings, in the first image chain B1, a first image sensor raw dataset RO1 and in the second image chain B2, a second image sensor raw dataset RO2 are present. The other steps of the second alternative of the method correspond for the first image chain B1 to the second step S21 and to the fourth step 31 of the first alternative and for the second image chain B2 to the third step S22 and the fifth step S32 of the second alternative. In this way, in the context of the first image chain B1, after carrying out the first image processing method, the first resultant image dataset E1 is obtained, which is designed and/or optimized for a human perception and in the context of the second image chain B2, after carrying out the second image processing method, the second resultant image dataset E2 is obtained which is designed and optimized for a further processing by machine. As in the first example, the two image processing methods differ and can comprise, in each case, a plurality of individual steps for example, a noise-reduction, a contrast processing, a filtration, a transformation etc.

If both the resultant image datasets are present, subsequently in a fourth step S31, in the context of the first image chain B1, the first resultant image dataset E1 is displayed—in the current example, as a 3D volume image—on a display unit, for example a monitor or a touch display. In this way, a user can analyze the 3D volume image and, if needed, carry out further actions.

In a fifth step S32 in the context of the second image chain B2, the second resultant image dataset E2 is passed on to an interface for further processing by machine in order to be fed to a unit for further processing by machine, said unit having, for example, a machine learning algorithm. In the present example, such a machine algorithm can comprise an automatic recognition of anatomical landmarks such as, for example, bone structures or vessel structures or lesions such as tumors or fractures. In an eighth step S33, in the context of the second image chain B2, the further processing by machine then takes place, that is, for example the automatic recognition of anatomical landmarks such as bone structures or vessel structures or lesions such as tumors or fractures. The processing result arising from the further processing by machine is then used in a ninth step S34 for controlling the medical imaging system. For example, using the recognition, a collimation of the collimator can be adapted to the actually relevant structures (important regions are included and unimportant regions are excluded). The machine recognition can also be used for further diagnosis or treatment.

The two alternatives of the method are usable for all possible applications. Apart from the examples given, for example, automatic localization of vessel occlusions or vessel stenoses can be recorded in preinterventional tomographic 3D volume images, for example, by computed tomography for an automatic navigation in endovascular robotic procedures (e.g. the CorPath GRX system from Corindus, Inc.), wherein the physician simultaneously analyzes 3D volume images. An automatic recognition of tumors in tomographic 3D datasets can also be carried out, as can be utilized, for instance, with automatic navigation in robotically performed/supported needle ablation procedures, wherein here also the physician makes diagnoses on 3D volume images optimized for human perception.

Furthermore, the method is usable for a plurality of different applications (e.g. for 2D, 3D and also 4D imaging), wherein simultaneously a manual use and a machine use (e.g. by an AI) are provided.

Apart from two different image chains as shown in FIGS. 1 and 2, a single image chain with different parameterization can be used for the image processing, that is, a first parameterization which generates from the image sensor raw dataset a first resultant image dataset which is configured for a human perception and a second parameterization which generates from the image sensor raw dataset a second resultant image dataset which is configured for a further processing by machine.

Further examples of the use of the method can be the following:

In X-ray fluoroscopy, by image processing by machine, for example, instruments or anatomical landmarks can be recognized and the result of the recognition can be used for control for setting parameters such as image refresh rates, X-ray voltage, X-ray current or prefiltering for improving image quality and dose efficiency. The first resultant image dataset is output to a display.

In angiography, a 3D dataset can be evaluated by image processing by machine with regard to an optimum projection direction for observing a vessel (e.g. a perpendicular viewing direction toward a vessel origin) and controlled for adjusting in this projection direction. The first resultant image dataset is output on a monitor.

In the case of an X-ray device with which a robotic system (lightweight robot with instrument holders) for carrying out percutaneous interventions such as needle ablations is associated, the robotic system can be controlled by analysis by machine of X-ray fluoroscopy images in real time. The first resultant image dataset is output on a monitor.

Figure 3:
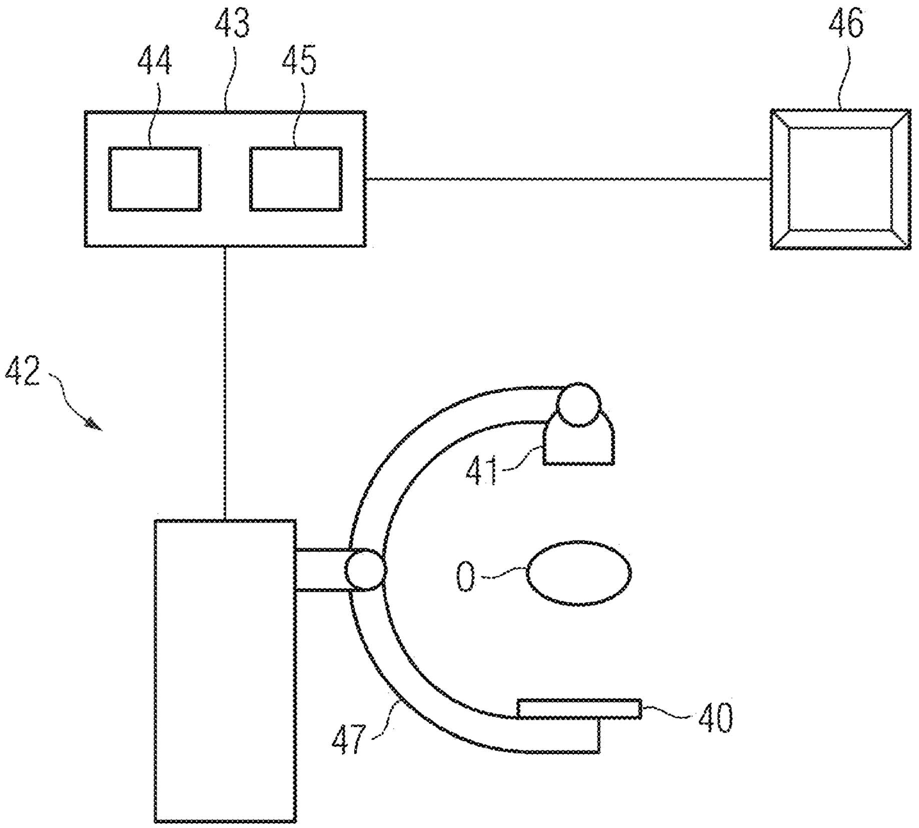
FIG. 3 is a view of a medical imaging system a method according to an example embodiment.

In FIG. 3, an X-ray device 42 is shown with a C-arm 47 and a robot system 49. Arranged on the C-arm 47 of the X-ray device 42 are an image sensor in the form of an X-ray detector 40 and an X-ray source 41 and the C-arm 47 is adjustable, for example, in a plurality of directions. A control unit 43 is provided for controlling the X-ray device 42. With this, the method according to example embodiments of the present invention can be carried out. The X-ray detector is configured for recording image sensor raw data. In addition, a processing unit 44 is provided for processing the image sensor raw data to a first resultant image dataset for a human perception and a second resultant image dataset for further processing by machine. The first resultant image dataset can be displayed for a user on a display unit 46 (e.g. a monitor). In addition, a unit 45 is provided for further processing by machine of the second resultant image dataset, in particular by an AI and/or a machine learning algorithm.

Figure 4:
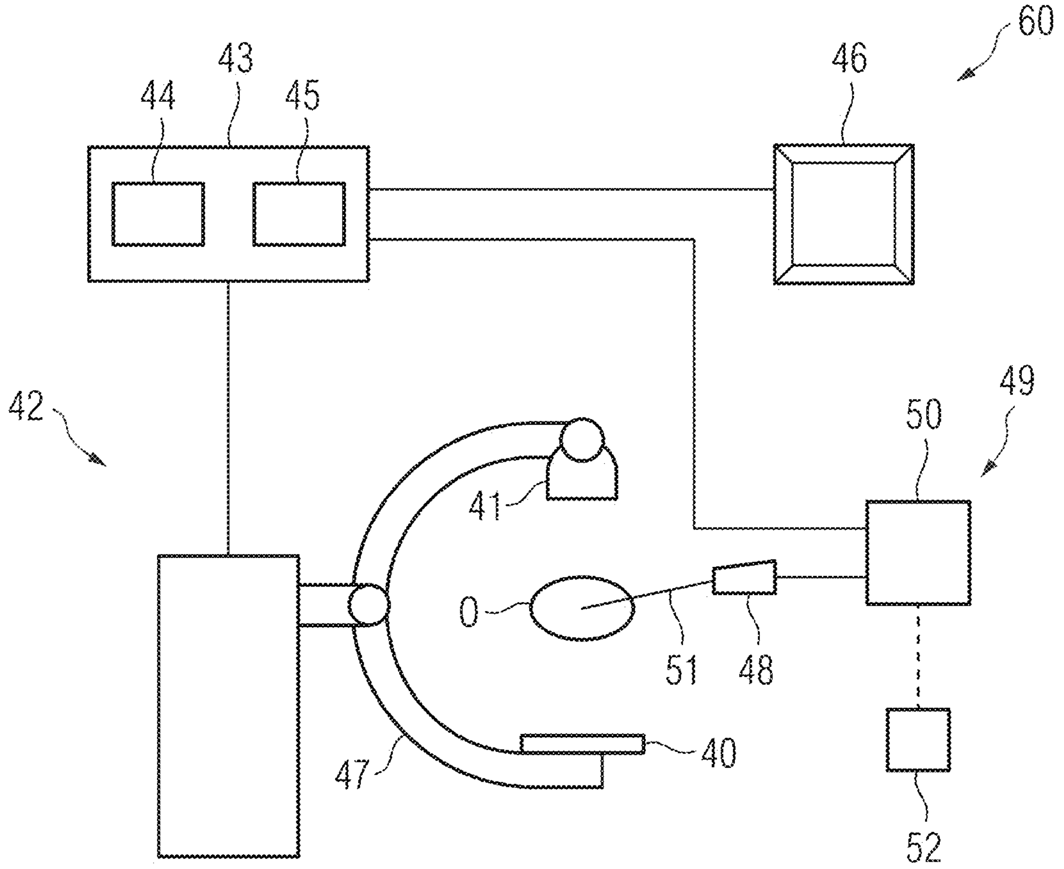
FIG. 4 is a view of a complete medical system a method according to an example embodiment.

In FIG. 4, a complete medical system 60 is shown, having an X-ray device 42 with a C-arm 47 and a robot system 49. Arranged on the C-arm 47 of the X-ray device 42 are an image sensor in the form of an X-ray detector 40 and an X-ray source 41, and the C-arm 47 is adjustable, for example, in a plurality of directions. A control unit 43 is provided for controlling the X-ray device 42. The robot system 49 has a robot control unit 50 which controls a drive system 48 for navigating an instrument, for example a catheter 51, in an organ O, for example a hollow organ, of a patient, wherein the robot control unit can receive input commands from an input unit 52. The robot system 49 is designed for navigation of an instrument in a hollow organ of a patient, executable robotically or robot-assisted and image-monitored, by the X-ray device 42. The method according to example embodiments of the present invention can be carried out by the complete system 60. The X-ray detector is designed for recording image sensor raw data. In addition, the complete system has a processing unit 44 for processing the image sensor raw data to a first resultant image dataset configured for a human perception and a second resultant image dataset configured for further processing by machine. The first resultant image dataset can be displayed for a user on a display unit 46 (e.g. a monitor). Furthermore, a unit 45 is provided for further processing by machine of the second resultant image dataset by a machine learning algorithm. The further processed data can then be used for controlling the navigation.

Apart from an X-ray system (2D X-ray system, 3D X-ray system, CT), the method can also be applied to another imaging system, for example, for an MRT, an ultrasonic device or a SPECT.

An extension to other medical sensor data as image data is also possible. All the data that is obtained by a sensor apparatus, the properties of which can be parameterized with regard to the data acquisition and/or the output of which can be subjected to a configurable post-processing can be used. An example thereof is acoustic signals which are recorded by a microphone. Also conceivable are non-medical image data which is used, for instance, in the context of non-destructive materials testing, for example, by CT, MR or ultrasound.

Thus, for example, in magnetic resonance angiography by analysis by machine of image datasets with regard to resolution and contrasts, a suitable sequence can be selected and adjusted in order to map the respective body region and/or the contrast medium distribution/flow dynamics therein as well as possible. In ultrasonic imaging also, after image analysis by machine, suitable frequencies and/or energies of the ultrasonic device can be controlled.

Example embodiments of the present invention provide: for a particularly good diagnosis and consequently treatment for a patient, a method is provided for recording and processing image sensor data of an examination object that can be generated by a medical imaging system, having the following steps: recording image sensor raw data of the examination object by way of an image detector of the imaging system, processing the image sensor raw data, wherein from the image sensor raw data, two resultant image datasets of the same examination object differing with regard to the image quality are created, wherein the image quality of a first resultant image dataset is configured for a human perception and the image quality of a second resultant image dataset is configured for a further processing by machine, and outputting the first resultant image dataset to a display unit and passing on the second resultant image dataset to an interface for further processing by machine and using a processing result arising from the second resultant image dataset by way of further processing by machine for controlling the medical imaging system or another medical system associated with the medical imaging system.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A method for recording and processing image sensor data of an examination object that is able to be generated by a medical imaging system, the method comprising:

recording image sensor raw data of the examination object using an image detector of the medical imaging system;

processing the image sensor raw data simultaneously via a first image processing method and a second image processing method to create two resultant image datasets of the examination object differing with regard to image quality, the first image processing method includes at least one of noise-reduction, contrast processing, filtration, or transformation of the image sensor raw data to generate a first resultant image dataset with an image quality configured for a human perception and the second image processing method includes at least one of noise-reduction, contrast processing, filtration, or transformation of the image sensor raw data to generate a second resultant image dataset with an image quality configured for further processing by a machine;

outputting the first resultant image dataset to a display unit;

providing the second resultant image dataset to an interface for further processing by a machine; and using a processing result arising from the second resultant image dataset, the processing result being generated from the further processing by the machine, wherein the first resultant image dataset has at least one of a lower noise level than the second resultant image dataset, a lower spatial resolution than the second resultant image dataset, or a lower image sharpness than the second resultant image dataset.

2. The method as claimed in claim 1, wherein an image sensor raw dataset is recorded and the first resultant image dataset and the second resultant image dataset are generated from a same recorded image sensor raw dataset using the first image processing method and the second image processing method, the first image processing method being different from the second image processing method.

3. The method as claimed in claim 1, wherein two image sensor raw datasets of the examination object are recorded in a same examination situation with different recording parameters, the first image processing method generates the first resultant image dataset from a first image sensor raw dataset and the second image processing method generates the second resultant image dataset from a second image sensor raw dataset.

4. The method as claimed in claim 1, wherein the medical imaging system includes an X-ray device and the image detector includes an X-ray detector.

5. The method as claimed in claim 3, wherein the recording parameters are based on at least one of, an X-ray voltage, an X-ray current, a pulse width of an X-ray pulse of an X-ray source, a filter setting of an X-ray collimator, a zoom setting of an image system, or a recording frequency.

6. The method as claimed in claim 1, wherein the image quality of at least one of the first resultant image dataset or the second resultant image dataset is determined by at least one of a signal-to-noise ratio, a contrast dynamic, an image sharpness, a spatial resolution, or an edge sharpness.

7. The method as claimed in claim 1, wherein the medical imaging system includes an angiography X-ray system, a fluoroscopy X-ray system, a computed tomography system, a magnetic resonance tomography system or an ultrasonic system.

8. A medical imaging system configured to perform the method of claim 1, the medical imaging system comprising:

a control unit configured to control the medical imaging system;

an image sensor configured to record the image sensor raw data of the examination object;

a processing unit configured to process the image sensor raw data to the first resultant image dataset and the second resultant image dataset;

the display unit configured to output the first resultant image dataset; and a unit configured to perform the further processing.

9. The medical imaging system as claimed in claim 8, wherein the control unit is configured to control at least some functions of the medical imaging system automatically.

10. A complete medical system including an imaging system configured to perform the method of claim 1 and a robot system configured to navigate an instrument in a hollow organ of a patient and image-monitored by the imaging system, the complete medical system comprising:

a control unit configured to control the imaging system;

an image sensor configured to record the image sensor raw data;

a processing unit configured to process the image sensor raw data to the first resultant image dataset and the second resultant image dataset;

a robot control system configured to control a robot-assisted drive system;
an input unit configured to receive an input;
the display unit configured to output the first resultant image dataset; and
a unit configured to perform the further processing using a machine learning algorithm, wherein the further processed data is used for controlling the navigation.

11. A method for recording and processing sensor data that is able to be created by a complete medical system, the method comprising:
recording sensor raw data using a sensor apparatus of the complete medical system;
processing the sensor raw data simultaneously via a first image processing method and a second image processing method to create two resultant image datasets of a same examination situation differing with regard to an image quality, the first image processing method includes at least one of noise-reduction, contrast processing, filtration, or transformation of the sensor raw data to generate a first resultant image dataset with an image quality configured for a human perception and the second image processing method includes at least one of noise-reduction, contrast processing, filtration, or transformation of the sensor raw data to generate a second resultant image dataset with an image quality configured for further processing by a machine;
outputting the first resultant image dataset to a display unit;
providing the second resultant image dataset to an interface for further processing by a machine; and
using a further processing result arising from the second resultant image dataset, the further processing result being generated from the further processing by the machine,
wherein the first resultant image dataset has at least one of a lower noise level than the second resultant image dataset, a lower spatial resolution than the second resultant image dataset, or a lower image sharpness than the second resultant image dataset.

12. The method as claimed in claim 11, wherein the first image processing method is different from the second image processing method.

13. The method as claimed in claim 11, wherein two sensor raw datasets of an examination object are recorded with different recording parameters, the first image processing method generates the first resultant image dataset from a first image sensor raw dataset and the second image processing method generates the second resultant image dataset from a second image sensor raw dataset.

14. The method as claimed in claim 2, wherein the medical imaging system includes an X-ray device and the image detector includes an X-ray detector.

15. The method as claimed in claim 3, wherein the medical imaging system includes an X-ray device and the image detector includes an X-ray detector.

16. The method as claimed in claim 4, wherein recording parameters are based on at least one of,
an X-ray voltage,
an X-ray current,
a pulse width of an X-ray pulse of an X-ray source,
a filter setting of an X-ray collimator,
a zoom setting of an image system, or
a recording frequency.

17. The method as claimed in claim 2, wherein the image quality of at least one of the first resultant image dataset or the second resultant image dataset is determined by at least one of
a signal-to-noise ratio,
a contrast dynamic,
an image sharpness,
a spatial resolution, or
an edge sharpness.

18. The method as claimed in claim 3, wherein the image quality of at least one of the first resultant image dataset or the second resultant image dataset is determined by at least one of
a signal-to-noise ratio,
a contrast dynamic,
an image sharpness,
a spatial resolution, or
an edge sharpness.

19. The method as claimed in claim 2, wherein the medical imaging system includes an angiography X-ray system, a fluoroscopy X-ray system, a computed tomography system, a magnetic resonance tomography system or an ultrasonic system.

20. The method as claimed in claim 3, wherein the medical imaging system includes an angiography X-ray system, a fluoroscopy X-ray system, a computed tomography system, a magnetic resonance tomography system or an ultrasonic system.

* * * * *